United States Patent [19]

Kritzler et al.

[11] 4,350,573

[45] Sep. 21, 1982

[54] HALOGENATED AROMATIC AMINES WHICH ARE STABLE IN COLOR, AND A PROCESS FOR THEIR PREPARATION

[75] Inventors: Helmuth Kritzler, Odenthal; Walter Böhm; Ulrich Kappler, both of Leverkusen, all of Fed. Rep. of Germany; Hans D. Winkelmann, Charleston, S.C.

[73] Assignee: Bayer Aktiengesellschaft, Leverkusen, Fed. Rep. of Germany

[21] Appl. No.: 200,843

[22] Filed: Oct. 27, 1980

[30] Foreign Application Priority Data

Nov. 14, 1979 [DE] Fed. Rep. of Germany ....... 2945868

[51] Int. Cl.³ .............................................. B01D 3/14

[52] U.S. Cl. ................................. 203/86; 202/267 R
[58] Field of Search ......... 203/86; 202/267 A, 267 R; 564/5–7

[56] References Cited

U.S. PATENT DOCUMENTS 3,274,077 9/1966 Hoffenberg et al. ................. 203/86

Primary Examiner—Frank Sever
Attorney, Agent, or Firm—Sprung, Horn, Kramer & Woods

[57] ABSTRACT

Halogenated aromatic amines are rendered colorstable by distillation and/or storing in equipment made of a rustproof material such as a Cr/Ni/Mo steel, tin, zinc, enamel, glass and/or ceramic material.

14 Claims, No Drawings

HALOGENATED AROMATIC AMINES WHICH ARE STABLE IN COLOR, AND A PROCESS FOR THEIR PREPARATION

The present invention relates to halogenated aromatic amines which are stable in colour, and to a process for their preparation.

It is known that the preparation of colourless aromatic amines presents difficulties (German Auslegeschrift No. 1,518,107). Even aromatic amines which appear colourless immediately after their preparation frequently discolour after a short time and are thus very often no longer suitable for further processing, for example to dyestuffs, since they change the properties of the products.

Compounds which can be added to the aromatic amines in very small amounts and which are supposed to prevent the discolouration of the aromatic amines during storage or at least suppress it for a relatively long time have thus been sought.

A number of "colour stabilisers" which are said to prevent discolouration of aromatic amines are described in the literature. Examples of suitable "colour stabilisers" which are mentioned are: hydrazine or hydrazine compounds (German Auslegeschrift No. 1,518,107 and U.S. Pat. No. 1,973,724), the reaction product of $P_2S_5$ and a polyalkyl-phenol U.S. Pat. No. 2,510,849), carbon disulphide (U.S. Pat. No. 2,434,651), 2-alkyl-alkoxy-phenols (U.S. Pat. No. 2,442,457), xylyl biguanides (U.S. Pat. No. 2,469,745) and thiocarbanilides (U.S. Pat. No. 2,493,544).

It was found, however, that halogenated aromatic amines to which stabilizers had been added led to coloured secondary products on further processing. Thus, for example, o-chloroaniline stabilized with hydrazine hydrate is unsuitable for the preparation of 3,3'-dichloro-4,4'-diamino-diphenylmethane, an important curing agent for polyurethane elastomers which are capable of being cast.

A process has now been found for the preparation of halogenated aromatic amines which are stable in colour, which is characterized in that the halogenated aromatic amines prepared in the customary manner are distilled in equipment made of rustproof materials and, if appropriate, the distilled halogenated aromatic amines are stopped and transported in containers made of rustproof materials.

The halogenated aromatic amines can be prepared by the reduction with iron (U.S. Pat. No. 2,143,152) or by the catalytic hydrogenation of the corresponding halogenated aromatic nitro compounds (J.Amer.Chem.Soc. 61, 3561 (1939)).

Possible rustproof materials are those which do not contain iron, or, if they do contain iron, it does not react with the halogenated aromatic amines. Examples of rustproof materials which can be used are: noble metal steels, such as Cr/Ni/Mo steels, metal alloys, such as nickel, lead, copper, tin, zinc and titanium alloys, pure or almost pure metals, such as nickel, copper, lead, tin, zinc and titanium, and nonmetallic materials, such as enamel, glass and ceramic materials. Cr/Ni/Mo steels, tin, zinc, enamel, glass and/or ceramic materials are preferably used as the rustproof materials.

Equipment made of Cr/Ni/Mo steels is particularly preferred. The compositions and names of the Cr/Ni/Mo steels are in some cases given in the nomenclature systems of various countries, for example in the German system DIN 17,440 and in the American system ASTM-A 167-74, ASTM-A 479-75 and ASTM-A 666-72.

Equipment which is particularly suitable for the process according to the invention is that made of Cr/Ni/Mo steels with the following composition (in % by weight): carbon: ≦0.10, silicon: 1.0, manganese: 2.0, chromium: 16.5 to 18.5, molybdenum: 2.0 to 2.5, nickel: 10.5 to 13.5 and titanium ≧5 times %C (material number 1.4571; DIN 17,440); or of the following composition: carbon: ≦0.04, manganese: ≦2.0, chromium: 16.5 to 18.5, molybdenum: 4.0 to 5.0, nickel: 12.5 to 14.5 and nitrogen: 0.10 to 0.20 (material number 1.4439; Stahl-Eisen-Werkstoffblatt 400, page 8, 4th edition, December 1973).

Compounds of the general formula

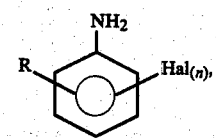

in which

R represents hydrogen, alkyl, alkoxy or halogen,

Hal denotes fluorine, chlorine or bromine, preferably chlorine or bromine, and n represents 1 or 2, may be mentioned as halogenated aromatic amines which can be used in the process according to the invention.

Possible alkyl radicals have up to 4 C atoms, preferably up to 2 C atoms. Examples which may be mentioned are: methyl, ethyl, n-propyl, iso-propyl, n-butyl, iso-butyl and tert.-butyl, preferably methyl and ethyl.

Possible alkoxy radicals have up to 4 C atoms, preferably up to 2 C atoms. Examples which may be mentioned are: methoxy, ethoxy, propoxy and butoxy, preferably methoxy and ethoxy.

Possible halogens are fluorine, chlorine and bromine, preferably chlorine.

Halogenated aromatic amines which may be mentioned are: 2-chloro-4-aminotoluene, 2-chloro-4-ethylaniline, 2-amino-4-chloroanisole, 2-amino-4-chlorophenetole, 2,5-dichloroaniline, o-bromoaniline, o-chloroaniline and m-chloroaniline, preferably o-chloroaniline, m-chloroaniline, 2,5-dichloroaniline and o-bromoaniline.

o-Chloroaniline is particularly preferably employed in the process according to the invention.

The process according to the invention can be carried out under normal pressure or under reduced pressure. The amines are preferably distilled under reduced pressure. The distillation is in general carried out under pressures of 1 mbar to normal pressure, preferably under 5 mbars to 35 mbars.

The distillation temperature depends on the particular pressure applied and is usually 70° to 250° C., preferably 80° to 100° C.

It has proved appropriate to distil the halogenated aromatic amines immediately after they have been prepared.

If the distilled halogenated aromatic amines according to the invention are to be stored for a relatively long time, it is advantageous to use containers made from the abovementioned rustproof materials.

Containers made of rustproof materials are also recommended for transportation of the halogenated aromatic amines.

Discolouration of the halogenated aromatic amines at a later date is thereby prevented.

The present invention also relates to halogenated aromatic amines which are stable in colour and can be obtained by distillation of halogenated aromatic amines, prepared in the customary manner, in equipment made of rustproof materials.

The colour of the halogenated aromatic amines treated by the process according to the invention is exceptionally stable, that is to say the amines retain their colourless characteristics for months if they are stored and transported in containers made of rustproof materials.

Aromatic amines prepared in the common manner tend to discolour after a short period of time (German Auslegeschrift No. 1,973,724, U.S. Pat. No. 4,510,849).

In contrary to this, the halogenated aromatic amines prepared according to the inventive process remain colour stable for at least 5 months. The colour stability of the halogenated aromatic amines has been determined by the Hazen colour number in accordance with the method of DIN No. 53,409.

Even after storage for a relatively long period, the amines can be used directly, without prior purification and/or distillation, for example for further processing to dyestuffs or to curing agents for polyurethanes.

It is exceptionally surprising that the colour stability of the halogenated aromatic amines can be achieved by simple distillation.

It is no longer necessary to add special "colour stabilisers", which may interfere in the further processing of the halogenated aromatic amines.

EXAMPLE o-Chloroaniline was prepared from o-nitrochlorobenzene by customary methods, by catalytic hydrogenation with platinum-on-charcoal in toluene, and, after separating off the catalyst and distilling off the toluene, was distilled, at a temperature of 78° C. and under a pressure of 5 mbars, in an apparatus made of Cr/Ni/Mo steel containing 16.5 to 18.5% of chromium, ≦0.10% of carbon, 1.0% of silicon, 2.0% of manganese, 2.0 to 2.5% of molybdenum, 10.5 to 13.5% of nickel and ≧5% of titanium.

The freshly distilled o-chloroaniline had a Hazen colour number of 40 (determination of the Hazen colour number in accordance with the method of DIN No. 53,409) and was stored at 20° C., in containers made of various materials, for a period of 5 months (Table 1).

TABLE 1

| Material of the container | Hazen color number | | | | | |
|---|---|---|---|---|---|---|
| | immediately after distillation | after 1 month | after 2 months | after 3 months | after 4 months | after 5 months |
| Iron (comparison) | 40 | 160 | 260 | >500[1] | >500 | >500 |
| Cr/Ni/Mo steel material No. 1.4571 (DIN 17,440) | 40 | 40 | 40 | 40 | 40 | 40 |
| Cr/Ni/Mo steel material No. 1.4439 (Stahl-Eisen-Werkstoffblatt 400, page 8) | 40 | 40 | 40 | 40 | 40 | 40 |
| Zinc | 40 | 70 | 80 | 90 | 90 | 100 |
| Dark brown glass | 40 | 40 | 40 | 40 | 50 | 60 |
| Glazed ceramic | 40 | 40 | 40 | 40 | 40 | 50 |

[1] The Hazen colour scale only goes up to 500.

What is claimed is:

1. A halogenated aromatic amine which is stable in color, said halogenated aromatic amine obtained by a process wherein an aromatic amine is recovered by distillation, the distillation being carried out in equipment made of a rustproof material.

2. In a process for the preparation of a halogenated aromatic amine, the improvement wherein the halogenated aromatic amine is one which is stable in color, which comprises recovering said halogenated aromatic amine from a reaction mixture by distillation in equipment made of a rustproof material.

3. A process according to claim 2 wherein following distillation the halogenated aromatic amine is stored in a container made of a rustproof material.

4. A process according to claim 3 wherein the halogenated aromatic amine is stored in equipment made of Cr/Ni/Mo steel, tin, zinc, enamel, glass and/or ceramic material.

5. A process according to claim 4 wherein the halogenated aromatic amine is stored in equipment made of Cr/Ni/Mo steel.

6. A process according to claim 3 wherein the halogenated aromatic amine is stored in equipment made of tin.

7. A process according to claim 3 wherein the halogenated aromatic amine is stored in equipment made of zinc.

8. A process according to claim 3 wherein the halogenated aromatic amine is stored in equipment made of enamel.

9. A process according to claim 2 wherein the halogenated aromatic amine is distilled in equipment made of Cr/Ni/Mo steel, tin, zinc, enamel, glass or a ceramic material.

10. A process according to claim 9 wherein the halogenated aromatic amine is distilled in equipment made of Cr/Ni/Mo steel.

11. A process according to claim 2 wherein the halogenated aromatic amine is ortho-chloro aniline.

12. A process according to claim 2 wherein the halogenated aromatic amine is distilled in equipment made of tin.

13. A process according to claim 2 wherein the halogenated aromatic amine is distilled in equipment made of zinc.

14. A process according to claim 2 wherein the halogenated aromatic amine is distilled in equipment made of enamel.

* * * * *